US012582707B2

(12) United States Patent
Shin et al.

(10) Patent No.: US 12,582,707 B2
(45) Date of Patent: Mar. 24, 2026

(54) IN-VITRO TRANSCRIPT MRNA AND PHARMACEUTICAL COMPOSITION COMPRISING SAME

(71) Applicants: ABION INC., Seoul (KR); SEOUL NATIONAL UNIVERSITY R&DB FOUNDATION, Seoul (KR)

(72) Inventors: Young Key Shin, Seoul (KR); Jun Young Choi, Gyeonggi-do (KR); Na Young Kim, Gyeonggi-do (KR); Wonrak Son, Gyeonggi-do (KR); Yong Jin Lee, Seoul (KR)

( * ) Notice: Subject to any disclaimer, the term of this patent is extended or adjusted under 35 U.S.C. 154(b) by 817 days.

(21) Appl. No.: 17/905,830

(22) PCT Filed: Mar. 17, 2021

(86) PCT No.: PCT/KR2021/003281
§ 371 (c)(1),
(2) Date: Sep. 8, 2022

(87) PCT Pub. No.: WO2021/187883
PCT Pub. Date: Sep. 23, 2021

(65) Prior Publication Data
US 2024/0226258 A1     Jul. 11, 2024

(30) Foreign Application Priority Data
Mar. 17, 2020     (KR) ........................ 10-2020-0032466

(51) Int. Cl.
| | |
|---|---|
| *A61K 39/02* | (2006.01) |
| *A61K 39/00* | (2006.01) |
| *C12N 15/85* | (2006.01) |

(52) U.S. Cl.
CPC .............. *A61K 39/02* (2013.01); *A61K 39/00* (2013.01); *C12N 15/85* (2013.01); *A61K 2039/53* (2013.01)

(58) Field of Classification Search
CPC .................................................... A61K 39/023
See application file for complete search history.

(56) References Cited

U.S. PATENT DOCUMENTS

2019/0290742 A1     9/2019   Chakraborty et al.

FOREIGN PATENT DOCUMENTS

| | | |
|---|---|---|
| EP | 3594337 A1 | 1/2020 |
| JP | 2015535430 A | 12/2015 |
| JP | 2018530332 A | 10/2018 |
| KR | 1020180057647 A | 5/2018 |

(Continued)

OTHER PUBLICATIONS

Sement, Jun. 2013, Nucleic Acids Research, vol. 41, No. 14, pp. 7115-7127 (Year: 2013).*

(Continued)

*Primary Examiner* — Mark L Shibuya

(57) ABSTRACT

The present invention relates to an RNA in-vitro transcript mRNA for intracellular expression of a gene of interest and a pharmaceutical composition comprising same for vaccines. When injected into animal cells, the in-vitro transcript mRNA including the gene of interest according to the present invention allows the protein of interest to be expressed in the animal cell in large quantities, and, as such, can be used as a gene vaccine against autoimmune diseases, infectious diseases, cancer- or tumor-related diseases, inflammatory diseases, and so on.

10 Claims, 6 Drawing Sheets

Specification includes a Sequence Listing.

(56) References Cited

FOREIGN PATENT DOCUMENTS

| KR | 1020180127360 A | 11/2018 | |
| WO | 2013071047 A1 | 5/2013 | |
| WO | 2013151666 A2 | 10/2013 | |
| WO | WO 2016/005324 * | 1/2016 | ............ C12N 15/09 |
| WO | 2-19121803 A1 | 6/2019 | |
| WO | WO 2019/121803 A1 * | 6/2019 | ............ C12N 15/67 |

OTHER PUBLICATIONS

Munoz-Tello, Jan. 2015, BioMed Research International, Issue 1, pp. 1 to 12 (Year: 2015).*

Chang, H., et al., "Tail-seq: Genome-wide Determination of Poly(A) Tail Length and 3 End Modifications", Molecular Cell, 2014, pp. 1044-1052, vol. 53, Publisher: Cell Press.

Ferizi, M., et al., "Human cellular CYBA UTR sequences increase mRNA translation without affecting the half-life of recombinant RNA transcripts", Scientific Reports, 2016, DOI:10.1038/srip39149, vol. 6, No. 39149, Publisher: www.nature.com/scientificreports.

Lee, M. H., "Development of nucleic acid vaccine platform against Anthrax toxin", Graduate Thesis for the Graduate School Convergence Science and Technology, Seoul National University, 2019, Publisher: Department of Molecular Mediine and Biopharmaceutical Science.

Notice of Allowance in Korean Patent Application No. 1020200032466 issued on Sep. 2, 2022, Sep. 2, 2022.

English Translation of Notice of Allowance in Korean Patent Application No. 1020200032466 issued on Sep. 2, 2022, Sep. 2, 2022.

Office Action issued on Jan. 14, 2021 in Korean Patent Application No. 1020200032466, Jan. 14, 2021.

Office Action issued on Oct. 5, 2022 in Korean Patent Application No. 1020200032466, Oct. 5, 2022.

English Translation of Office Action issued on Oct. 5, 2022 in Korean Patent Application No. 1020200032466, Oct. 5, 2022.

English Translation of Office Action issued on Jan. 14, 2021 in Korean Patent Application No. 1020200032466, Jan. 14, 2021.

Pardi, N., et al., "mRNA vaccines—a new era in vaccinology", Nat Rev Drug Discov, 2018, pp. 261-279, vol. 17, No. 4, Publisher: HHS Public Access.

Steinle, H., et al., "Generation in iPSCs by Nonintegrative RNA-Based Reprogramming Techniques: Benefits of Self-Replicating RNA versus Synthetic mRNA", Stem Cells Inernational, 2019, https://doi.org/10.1155/2019/7641767, vol. 2019, No. 7641767, Publisher: Hindawi.

Search Report issued on Mar. 14, 2024 for European Patent Application 21771925.1.

Holtkamp, S., et al., "Modification of antigen-encoding RNA increases stability, translational efficacy, and T-cell stimulatory capacity of dendritic cells", Blood, 2006, pp. 4009-4017, vol. 108, Publisher: American Society of Hematology.

Office Action issued on Mar. 28, 2024 for Japanese Patent Application 2022-555835.

English Translation of Office Action issued on Mar. 28, 2024 for Japanese Patent Application 2022-555835.

Trepotec, Z., "Minimalistic 5'-UTRs and segmented poly(A) tails—a step towards increased potency of transcript therapies", Dissertation, 2019, pp. 42-68, Publisher: Faculty of Medicine of the Ludwig Maximilian University of Munich.

Office Action in Japanese Patent Application No. 2022-555835 on Oct. 17, 2023.

English Translation of Office Action in Japanese Patent Application No. 2022-555835 on Oct. 17, 2023.

Park, H-J, et al., "The Characteristics of RNA Vaccine: its Strengths and Weaknesses", Journal of Bacteriology and Virology, 2016, pp. 115-127, vol. 46, No. 3.

Sayour, E.J., et al., "Bridging infectious disease vaccines with cancer immunotherapy: a role for targeted RNA based immunotherapeutics", Journal for Immuno Therapy of Cancer, 2015, DOI 10.1186/s40425-015-0058-0, vol. 3, No. 13, Publisher: BioMed Central.

Wolff, J.A., et al., "Direct Gene Transfer into Mouse Muscle in Vivo", Science, 1990, pp. 1465-1468, vol. 247.

* cited by examiner

【Fig. 1】
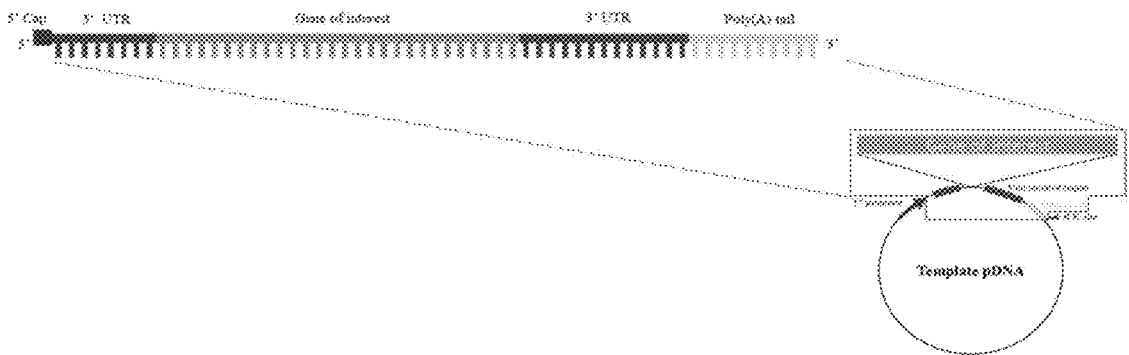

【Fig. 2】
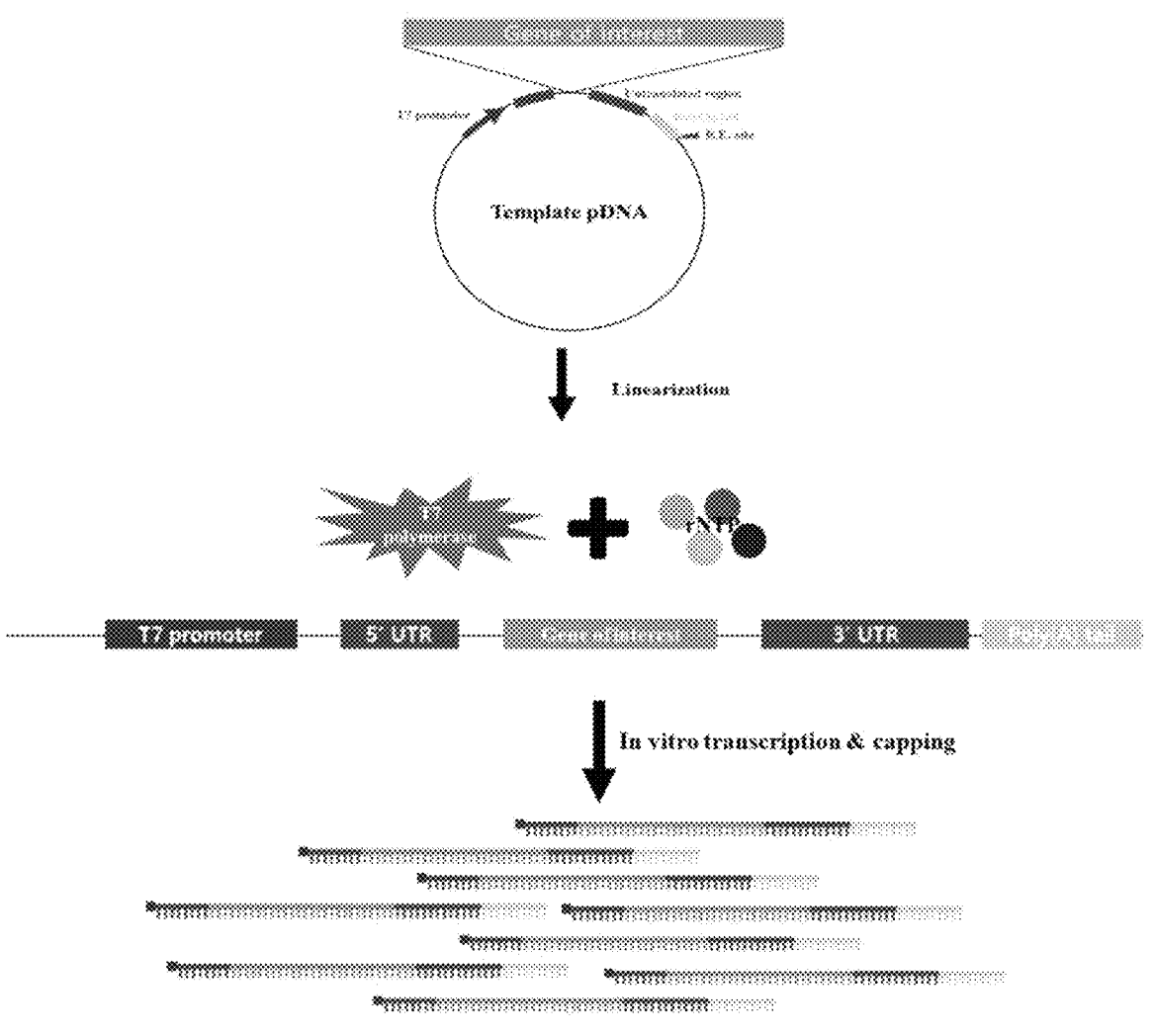
mRNA

【Fig. 3】
a
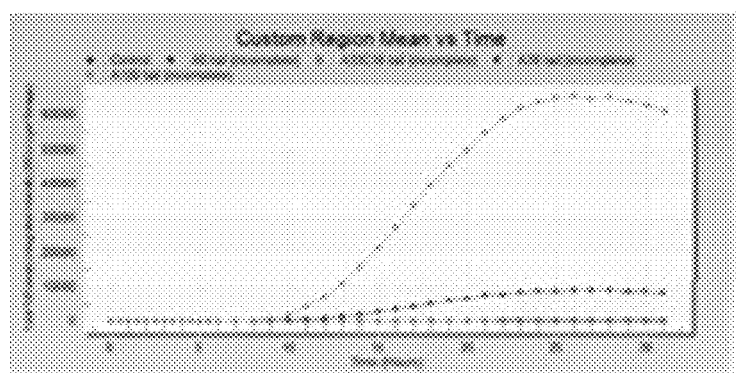
b
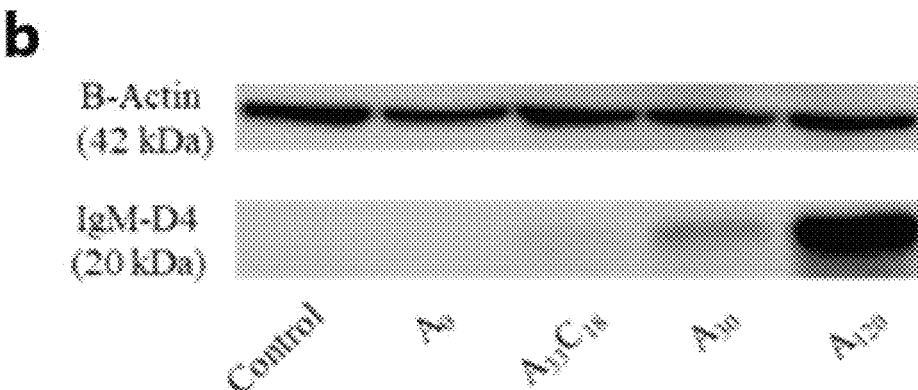
【Fig. 4】
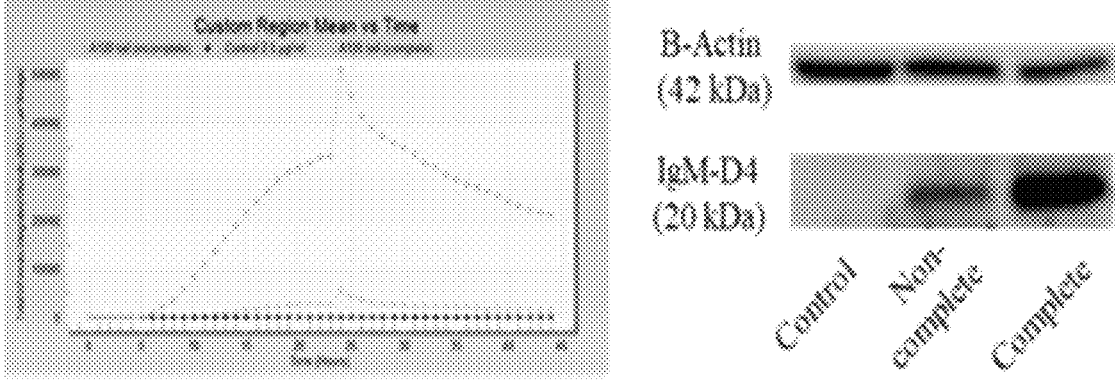

【Fig. 5】
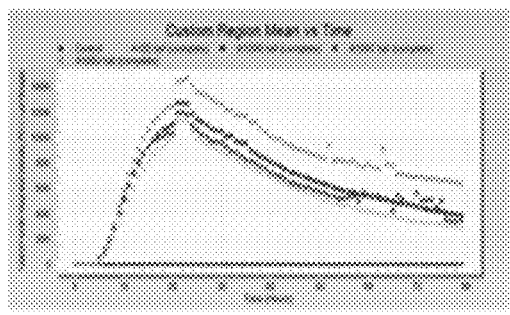
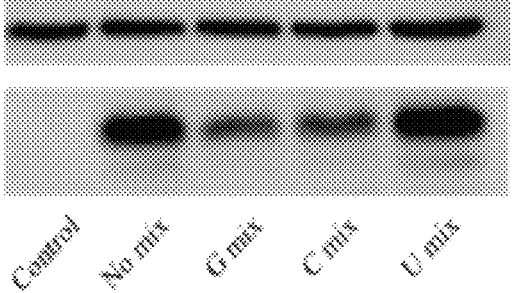

【Fig. 6】
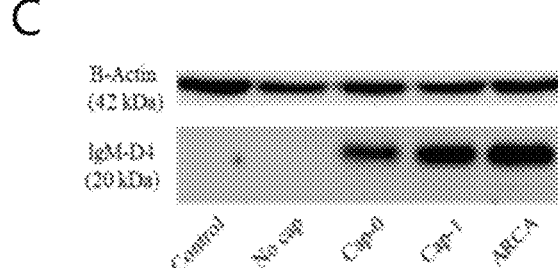
A
B¹ and B² = nucleobases
Cap 0: R¹ and R² = H
Cap 1: R¹ = Me and R² = H
Cap 2: R¹ and R² = Me
B
ARCA
C
β-Actin
(42 kDa)
IgM-D4
(30 kDa)

【Fig. 7】
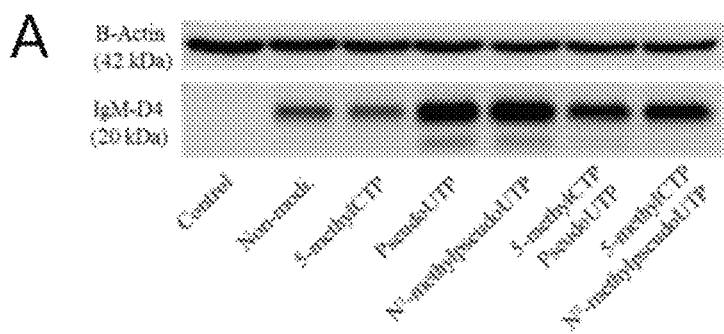
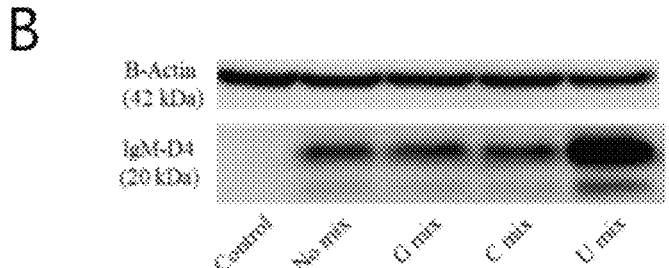

IN-VITRO TRANSCRIPT MRNA AND PHARMACEUTICAL COMPOSITION COMPRISING SAME

CROSS-REFERENCE TO RELATED APPLICATIONS

This is a U.S. national phase under the provisions of 35 U.S.C. § 371 of International Patent Application No. PCT/KR2021/003281 filed Mar. 17, 2021, which in turn claims priority under the provisions of 35 U.S.C. § 119 of Korean Patent Application No. 10-2020-0032466 filed Mar. 17, 2020. The disclosures of all such applications are hereby incorporated herein by reference in their respective entireties, for all purposes.

REFERENCE TO SEQUENCE LISTING

This application includes an electronically submitted sequence listing in .txt format. The .txt file contains a sequence listing entitled "648_UpdatedSeqListing_ST25.txt" created on Mar. 12, 2023 and is 7531 bytes in size. The sequence listing contained in this .txt file is part of the specification and is hereby incorporated by reference herein in its entirety.

TECHNICAL FIELD

The present invention relates to an in-vitro transcript mRNA for intracellular expression of a gene of interest, and more particularly to an RNA in-vitro transcript mRNA for intracellular expression of a gene of interest and a pharmaceutical composition for a vaccine including the same.

BACKGROUND ART

Genetic therapies and genetic vaccines are technologies that have already been proven and broadly applied in the pharmaceutical field, and may be used not only for treatment of genetic diseases, but also for treatment of autoimmune diseases, infectious diseases, cancer- or tumor-related diseases, inflammatory diseases, and the like.

Genetic vaccines have begun to be developed based on reports that, when DNA and RNA encoding a target gene are directly injected into an animal, the target gene is expressed in the living animal, thereby making it possible to realize immunity (Wolff J. A. et al. Science, 247:1465-8, 1990).

In genetic therapy or genetic vaccination, DNA and RNA may be used as nucleic acid molecules for gene administration, and it is known that DNA is more stable and easier to handle than RNA. In the case of DNA, however, a potential risk may arise when damage to the gene occurs due to insertion of the DNA fragment administered into the genome of a patient at an undesired location. Additionally, unwanted anti-DNA antibodies may appear, and moreover, the level of expression of the peptide or protein to be expressed by DNA administration and subsequent transcription/translation is limited, which is undesirable. The presence or absence of a specific transcription factor that regulates DNA transcription has a major influence on the expression level of the administered DNA, and in the absence of a specific transcription factor, a sufficient amount of RNA is not produced by DNA transcription, and consequently, the amount of the peptide or protein that is translated and produced is also limited.

On the other hand, when RNA is used for gene administration, RNA does not require transcription, and thus the protein may be synthesized directly in the cytoplasm without the need to enter the nucleus, like DNA, so there is no fear of causing unwanted genetic damage due to insertion into cell chromosomes. Moreover, RNA, having a shorter half-life than DNA, does not induce long-term genetic modification (Sayour E. J. et al., J. Immunother. Cancer 2015; 3:13, 2015). When a general RNA vaccine is delivered into cells, it is activated in a short time to thus express the target protein, and is destroyed by an enzymatic reaction within a few days, and the specific immune response to the expressed target antigen (protein) remains.

In addition, when is used for gene RNA administration, RNA acts by passing only through the cell membrane without the need to pass through the nuclear membrane, so RNA is capable of expressing the same amount of target protein as DNA even when used in a smaller amount than DNA. Also, since RNA itself has higher immune-enhancing properties, it is possible to exhibit the same immune effect even when administered in a smaller amount than DNA.

Furthermore, RNA may be mass-produced in vitro, so it may be safely produced even in a small-scale GMP production facility, and an RNA transcript may be produced in a manner in which only the gene of an epitope associated with induction of a neutralizing antibody of a virus or microorganism is synthesized and then transcribed in vitro. In the past, a lot of expense and sophisticated technology have been required to produce a large amount of RNA in this way, but it is now possible to produce a large amount of RNA within 1-2 weeks using a small amount of DNA template owing to improvements to reagents related to in-vitro transcription reactions, particularly DNA-dependent RNA polymerase.

A genetic vaccine is a system that expresses a target antigen by inoculating an animal with a gene (DNA or RNA) of a protein to be expressed using various vectors. Interestingly, the amount of the protein that is expressed by the gene is not directly proportional to immunogenicity in practice. Even when the amount of the antigen that is expressed is increased, it does not necessarily mean that the immunogenicity of the antigen also increases proportionally. In general, when a genetic vaccine is injected into an animal, the genetic vaccine (DNA or RNA) is delivered to and infects the animal muscle cells in various ways. Since the muscle cells thus infected are lysed by antigen-specific T cells, the actual antigen expression period or the amount of the antigen is not as predicted in in-vitro cell culture experiments. Therefore, further studies are needed to understand precisely how genetic vaccines induce immune responses through the limited expression level and period. In practice, the results obtained from in-vitro cell culture studies are often inconsistent with those obtained from in-vivo animal experiments. The reason is that there are a difference in the species-specific expression and antigen recognition pattern of the innate immune receptor involved in the immune response after administration of the genetic vaccine and also a difference in the expression level of the innate immune receptor by cell type. Rather than explaining that the self-replicon RNA vaccine based on an alpha virus has high antigenic immunogenicity simply due to the high antigen expression level, it suggests that there may be another influential factor (Park J. H. et al., *J. Bacteriol. & Virol.*, 46:115, 2016).

Therefore, in order to induce an excellent immune response by the gene of interest, the amount of protein expressed in the animal cells by the administered RNA, construction of the administered RNA transcript, the appropriate RNA dose required for immunity, and optimal RNA modification using a compound such as protamine are regarded as important (Park J. H. et al., *J. Bacteriol. & Virol.*, 46:115, 2016).

Accordingly, the present inventors have made great efforts to develop a method of stably expressing a gene of interest in animal cells, and ascertained that, when a gene of interest is delivered to animal cells using an in-vitro transcript mRNA including a gene of interest, 5'-UTR and 3'-UTR linked to both ends of the gene of interest, a 5' cap linked to 5'-UTR, and a poly(A) tail containing 20 to 400 adenines linked to 3'-UTR, a protein of interest may be produced with excellent expression efficiency in the animal cells, thus culminating in the present invention.

DISCLOSURE

It is an object of the present invention to provide an in-vitro transcript mRNA for stably expressing a gene of interest in animal cells.

It is another object of the present invention to provide a DNA template for producing the in-vitro transcript mRNA.

It is still another object of the present invention to provide a pharmaceutical composition for a vaccine including the in-vitro transcript mRNA.

In order to accomplish the above objects, the present invention provides an in-vitro transcript mRNA including (a) an RNA sequence insertion portion encoding a peptide of interest or a protein of interest, (b) 5'-UTR and 3'-UTR linked to both ends of the RNA sequence encoding the peptide of interest or the protein of interest, (c) a 5' cap linked to 5'-UTR, and (d) a poly(A) tail containing 20 to 400 adenine linked to 3'-UTR.

In addition, the present invention provides a template DNA for in-vitro transcript mRNA production including (a) a portion DNA having a sequence corresponding to the RNA in-vitro transcript mRNA and (b) a promoter to which RNA polymerase binds for transcription of the DNA sequence corresponding to the in-vitro transcript mRNA.

In addition, the present invention provides a pharmaceutical composition for a vaccine including the in-vitro transcript mRNA.

In addition, the present invention provides a method of preventing or treating a disease including administering the in-vitro transcript mRNA.

In addition, the present invention provides the usage of the in-vitro transcript mRNA for the prevention or treatment of a disease.

In addition, the present invention provides the use of the in-vitro transcript mRNA for the prevention or treatment of a disease.

DESCRIPTION OF DRAWINGS

FIG. 1 shows the configuration of an in-vitro transcript mRNA and a template DNA according to the present invention;

FIG. 2 shows a process of synthesizing the in-vitro transcript mRNA through in-vitro transcription from the template plasmid DNA according to the present invention;

FIG. 3 shows results confirming the expression level of a protein of interest depending on the length of the poly(A) tail of the in-vitro transcript mRNA;

FIG. 4 shows results confirming the expression level of the protein of interest depending on the shape of the end of the poly(A) tail of the in-vitro transcript mRNA;

FIG. 5 shows results confirming the expression level of the protein of interest depending on whether a non-A residue is mixed in the poly(A) tail of the in-vitro transcript mRNA;

FIG. 6 shows results confirming the expression level of the protein of interest depending on the type of cap of the in-vitro transcript mRNA; and FIG. 7 in part A thereof shows results confirming the expression level of the protein of interest by substituting a nucleotide of the in-vitro transcript mRNA with a modified nucleotide, and in part B thereof shows results confirming the expression level of the protein of interest by substituting the non-A residue of the non-A residue-mixed poly(A) tail with a modified nucleotide.

MODE FOR INVENTION

Unless otherwise defined, all technical and scientific terms used herein have the same meanings as those typically understood by those skilled in the art to which the present invention belongs. In general, the nomenclature used herein is well known in the art and is typical.

Although conventional genetic therapies already provide means for improved mRNA stabilization and translation activity, problems such as low stability of RNA-based platforms still remain. Therefore, it is necessary to develop a platform for improved mRNA stability and translation activity in order to provide a better expression level of the encoded protein in vivo, and the present invention proposes an in-vitro transcript mRNA including (a) an RNA sequence insertion portion encoding a peptide of interest or a protein of interest, (b) 5'-UTR and 3'-UTR linked to both ends of the RNA sequence encoding the peptide of interest or the protein of interest, (c) a 5' cap linked to 5'-UTR, and (d) a poly(A) tail containing 20 to 400 adenines linked to 3'-UTR (FIG. 1). The in-vitro transcript mRNA having the poly(A) tail ($A_{120}$) containing 120 adenines constructed through the method of the present invention stably exhibits a high expression level of a protein of interest in animal cells administered therewith, compared to mRNA having $A_{33}C_{18}$, $A_0$, and $A_{30}$ tails.

Accordingly, an aspect of the present invention pertains to an in-vitro transcript mRNA including (a) an RNA sequence insertion portion encoding a peptide of interest or a protein of interest, (b) 5'-UTR and 3'-UTR linked to both ends of the RNA sequence encoding the peptide of interest or the protein of interest, (c) a 5' cap linked to 5'-UTR, and (d) a poly(A) tail containing 20 to 400 adenines linked to 3'-UTR.

In the present invention, the gene of interest may be a gene encoding a therapeutically active protein or peptide, adjuvant protein, antigen, tumor antigen, pathogenic antigen, animal antigen, viral antigen, protozoan antigen, bacterial antigen, allergic antigen, autoimmune antigen, allergen, antibody, immunostimulatory protein or peptide, or antigen-specific T-cell receptor.

In the present invention, the 5' cap is a component located at the 5' start site of mRNA. The cap structure initiates protein synthesis and serves to protect mRNA from the action of nuclease. The 5' cap also affects translation. During initiation of translation, the 5' cap binds to eIF4E (eukaryote translation initiation factor 4 E) to thus attach a 40S ribosomal subunit to mRNA.

In the present invention, the 5' cap may be a Cap-1 or ARCA (anti-reverse cap analog).

In the present invention, when constructing a transcript through a co-transcriptional capping method for performing capping and transcription at the same time, ARCA-RNA was

5 synthesized using a mMESSAGE mMACHINE™ T7 ULTRA Transcription kit (Thermo Fisher Scientific).

Moreover, when performing a post-transcriptional capping method, uncapped RNA was synthesized using a MEGAscript™ T7 transcription kit (ThermoFisher Scientific).

In the present invention, in order to determine a 5' cap optimal for an in-vitro transcript mRNA platform for delivery of a gene of interest to animal cells and expression thereof, in-vitro transcript mRNA having no cap, Cap-0, Cap-1, or ARCA was synthesized, and the expression level of the protein of interest in 293T cells was compared, indicating that the expression efficiency of ACRA and Cap-1 was the greatest (FIG. 6). However, in the method for performing in-vitro transcription and capping at the same time by decreasing the GTP ratio and increasing the cap analog ratio like ARCA, uncapped RNA may be synthesized. This is capable of inducing innate immunity, so Cap-1, which is a post-transcriptional capping system using an enzyme, was determined to be more suitable for the in-vitro transcript mRNA platform.

In the present invention, it is preferable that a Kozak sequence be added upstream of the start codon of the gene of interest and that the gene of interest have a codon-optimized sequence for the host cell.

The poly(A) tail is a component located at the 3' end of the in-vitro transcript mRNA of the present invention. Along with the 5' cap, the poly(A) tail serves to protect mRNA from enzymatic degradation, and when the length thereof is insufficient, it is known that the stability of mRNA is deteriorated. The poly(A) tail also affects translation. PABP (poly(A)-binding protein), which is a protein that binds to the poly(A) tail, binds to eIF4G (eukaryote translation initiation factor 4 G) during initiation of translation to thus attach the 40S ribosomal subunit to mRNA.

In the present invention, the poly(A) tail may contain 20 to 400 adenines, preferably 30 to 200 adenines, more preferably 60 to 150 adenines, much more preferably 100 to 130 adenines.

In an embodiment of the present invention, in order to compare the translation efficiency of mRNA depending on changes in the length of the poly(A) tail, a template DNA having each of a conventional $A_{33}C_{18}$ tail, as well as $A_0$, $A_{30}$, and $A_{120}$ tails respectively containing 0, 30, and 120 adenines, was synthesized, after which mRNA produced through in-vitro transcription was introduced into 293T cells and the expression level of the protein of interest was compared. Consequently, IgM-D4 expression was not observed in the $A_0$ tail, and it was confirmed that expression was best for the $A_{120}$ tail, sequentially followed by the $A_{30}$ tail and the $A_{33}C_{18}$ tail (FIG. 3).

In the present invention, the poly(A) tail may be configured such that at least one non-adenine nucleotide selected from the group consisting of uracil (U), cytosine (C), and guanine (G) is inserted between a plurality of adenines. Here, the non-adenine nucleotide is inserted between 2 to 20, preferably 4 to 15, more preferably 6 to 12, most preferably 8 to 10 adenines, but the present invention is not limited thereto.

In an embodiment of the present invention, in order to compare the translation efficiency of the non-A residue-mixed tail, a template DNA having each of the original $A_{120}$ tail, $A_{120}$-G-mixed tail, $A_{120}$-C-mixed tail, and $A_{120}$-U-mixed tail was constructed. An in-vitro transcript mRNA was synthesized using each template, and the expression level of the protein of interest in 293T cells was compared in the same manner as in Example 3. Consequently, it was confirmed that the mRNA expression efficiency of the U-mixed tail was the greatest.

In the present invention, the end of the poly(A) tail may be adenine.

Since the linearized DNA template is used upon in-vitro transcription, the end of the poly(A) tail of mRNA that is produced may be terminated with residue A or may include a restriction enzyme recognition site, depending on the restriction enzyme used for linearization of the template plasmid DNA.

In order to compare the extent of translation depending on the shape of the end of the poly(A) tail, non-complete or complete end mRNA was synthesized based on a template linearized with an NheI or SapI restriction enzyme, and the expression level of the protein of interest was compared. Consequently, the expression efficiency of mRNA having a tail the end of which is terminated with A alone was determined to be higher (FIG. 4).

In the present invention, all or part of uracil (U) of the in-vitro transcript mRNA sequence may be substituted with modified U, and the modified UTP may be pseudo UTP or N1-methylpseudo UTP.

In the present invention, the poly(A) tail may be configured such that modified U is inserted between a plurality of adenines.

In an embodiment of the present invention, in order to determine a modified nucleotide suitable for the in-vitro transcript mRNA platform for delivery of a gene of interest to animal cells and expression thereof, in-vitro transcript mRNA including modified CTP or UTP was synthesized, and the expression level of the protein of interest in 293T cells was compared.

Consequently, it was confirmed that the protein expression efficiency of mRNA in which U of mRNA was 100% substituted with modified U using modified UTP alone was the highest (FIG. 7). Moreover, since it is judged that use thereof with the U-mixed tail having excellent protein expression efficiency is capable of exhibiting a synergistic effect, the results for the mixed tail using modified UTP were compared, and it was found that protein expression in the U-mixed tail was the greatest.

Another aspect of the present invention pertains to a template DNA for in-vitro transcript mRNA production including (a) a portion having a DNA sequence corresponding to the RNA in-vitro transcript mRNA and (b) a promoter to which RNA polymerase binds for transcription of the DNA sequence corresponding to the in-vitro transcript mRNA.

In the present invention, the promoter may be selected from the group consisting of a T7 promoter, a T3 promoter, and an SP6 promoter.

In the present invention, the template DNA may include a restriction enzyme recognition site that is linked to the poly(A) tail.

The restriction recognition site is preferably a sequence configured to terminate the end of the poly(A) tail of the in-vitro transcript mRNA with adenine (A) upon treatment with a restriction enzyme, and the restriction enzyme is preferably NheI or SapI.

In order to construct the in-vitro transcript mRNA of the present invention, since mRNA is produced through a general in-vitro transcription reaction, all production processes are performed in vitro. Specifically, since RNA is synthesized in vitro by T7, SP6, or T3 RNA polymerase using, as a template, DNA that is linearized after enzymatic cleavage of the end thereof, there is no need to directly handle live viruses or microorganisms used in the manufacture of common living or dead vaccines. Moreover, culture of yeast, *E. coli*, or insect cells, which must be used for the production of recombinant vaccines (recombinant proteins), is unnecessary.

Still another aspect of the present invention pertains to a pharmaceutical composition for a vaccine including the in-vitro transcript mRNA.

A gene of interest may be inserted into the in-vitro transcript mRNA of the present invention, and examples thereof may include genes respectively encoding a therapeutically active protein or peptide, adjuvant protein, antigen, tumor antigen, pathogenic antigen, animal antigen, viral antigen, protozoan antigen, bacterial antigen, allergic antigen, autoimmune antigen, allergen, antibody, immunostimulatory protein or peptide, and antigen-specific T-cell receptor, and depending on the type of gene that is inserted, the in-vitro transcript mRNA of the present invention may be used in a genetic vaccine for autoimmune diseases, infectious diseases, cancer- or tumor-related diseases, inflammatory diseases, and the like.

Yet another aspect of the present invention pertains to a method of preventing or treating a disease including administering the in-vitro transcript mRNA.

A further aspect of the present invention pertains to the usage of the in-vitro transcript mRNA for the prevention or treatment of a disease.

Still a further aspect of the present invention pertains to the use of the in-vitro transcript mRNA for the prevention or treatment of a disease.

The in-vitro transcript mRNA platform is innovative vaccine production technology that completely rejuvenates the current vaccine production method. Recently, there are many cases of outbreaks of viruses that have existed for some time but suddenly cause problems, for example new mutant viruses such as MERS virus, COVID-19, etc., or Zika virus. However, it is impossible in practice to always have vaccines ready for all of these sources of infection. In-vitro transcript mRNA is the only production platform that best meets conditions for crisis-response vaccination. In the production of mRNA, even when there is only a very small amount of template DNA, it is possible to produce 300,000 doses of RNA corresponding to the essential amount for the country within 1 to 2 weeks. This is because in-vitro production of mRNA does not require a biological reactor, and also because the in-vitro transcript mRNA platform of the present invention is the only vaccine production platform capable of producing a vaccine by synthetically processing all relevant genes without the need to directly respond to the source of infection.

A better understanding of the present invention may be obtained through the following examples. These examples are merely set forth to illustrate the present invention, and are not to be construed as limiting the scope of the present invention, as will be apparent to those skilled in the art.

Example 1: Construction of Template DNA

A template plasmid DNA (template pDNA) necessary as a template for in-vitro transcript mRNA production was constructed. The gene for the protein of interest that was used was a tomato fluorescent protein gene.

In order to insert the gene for the protein of interest into the template pDNA, the gene for the protein of interest was amplified through PCR using a pTdTomato-N1 vector including the tomato fluorescent protein gene (SEQ ID NO: 1) as a template.

When designing primers, 20 bp of both ends of the gene for the protein of interest were used as annealing sites, and PCR primers designed to add an EcoRI recognition sequence-Kozak sequence and a HindIII recognition sequence to both ends were used.

```
Forward primer:
                                    (SEQ ID NO: 3)
  5' at gaattc gccacc atggtgagcaagggcgagga 3'

Reverse primer:
                                    (SEQ ID NO: 4)
  5' at aagctt ttacttgtacagctcgtcca 3'
```

After PCR, the tomato fluorescent protein gene amplified through electrophoresis was identified and purified using a MEGAquick-spin™ plus Fragment DNA Purification Kit (iNtRON). Next, the in-vitro transcription template pDNA (SEQ ID NO: 2) and the tomato fluorescent protein DNA were cleaved using restriction enzymes EcoRI and HindIII (Thermo Fisher), purified using a MEGAquick-spin™ plus Fragment DNA Purification Kit, and then subjected to ligation using T4 ligase (Enzynomics).

After ligation, the plasmid was transformed into DH5a competent cells, followed by culture at 37° C. overnight, after which pDNA was isolated from the cultured colonies and the template pDNA sequence was identified by a sequencing service (Cosmo Genetech).

Example 2: In-Vitro Synthesis of mRNA

In-vitro transcript mRNA (transcript mRNA) was synthesized in vitro using the template plasmid DNA constructed in Example 1 as a template and using T7 RNA polymerase.

Specifically, the template plasmid DNA was linearized by performing cleaving downstream of the poly(A) tail using an NheI or SapI restriction enzyme (Thermo Fisher Scientific), and purified using a MEGAquick-Spin™ plus Fragment DNA Purification Kit (Intron) to obtain a template DNA, after which in-vitro transcription was performed using the template DNA thus obtained (FIG. 2).

When a transcript was constructed through a co-transcriptional capping method for performing capping and transcription at the same time, ARCA-RNA was synthesized using a mMESSAGE mMACHINE™ T7 ULTRA Transcription kit (ThermoFisher Scientific).

When a post-transcriptional capping method was performed, uncapped RNA was synthesized using a MEGAscript™ T7 transcription kit (Thermo Fisher Scientific). The experiment was carried out according to the kit's protocol, and the experimental method was as follows.

Specifically, solutions for the kit were added to 1 μg of the linearized template DNA as shown in Table 1 or Table 2 below, and a mixed solution having a final volume of 20 μL was prepared. When modified nucleotides such as 5-methyl-CTP, pseudo-UTP, and N1-methylpseudo-UTP (TriLink) were used, the nucleotide was 100% substituted with a modified nucleotide in consideration of the concentration.

TABLE 1

Mixed solution composition for reaction using
mMESSAGE mMACHINE ™ T7 ULTRA Transcription
kit for ARCA-RNA synthesis

| | |
|---|---|
| Linear template DNA | 1 μL |
| T7 enzyme mix | 2 μL |
| 10X T7 Reaction buffer | 2 μL |
| T7 2X NTP/ARCA | 10 μL |
| Nuclease free water | Up to 20 μL |

TABLE 2

Mixed solution composition for reaction using MEGAscript ™ T7
transcription kit for uncapped RNA synthesis

| | |
|---|---|
| Linear template DNA | 1 μg |
| T7 enzyme mix | 2 μL |
| 10X Reaction buffer | 2 μL |
| Enzyme mix | 2 μL |
| 75 mM ATP solution | 2 μL |
| 75 mM CTP solution | 2 μL |
| 75 mM GTP solution | 2 μL |
| 75 mM UTP solution | 10 μL |
| Nuclease free water | Up to 20 μL |

The mixed solution prepared above was allowed to react at 37° ° C. overnight, added with 1 μL of DNase, and allowed to react at 37° C. for 15 minutes, and finally, the synthesized in-vitro transcript RNA (SEQ ID NO: 5) was purified using lithium chloride*.

When the synthesized uncapped RNA was capped with Cap-0 and Cap-1, the experiment was carried out using a ScriptCap™ M7G Capping System kit (CELLSCRIPT) and a ScriptCap™ Cap-1 Capping System kit (CELLSCRIPT), respectively, according to the manufacturer's protocol. The experimental method was as follows.

Specifically, 55 μg of uncapped RNA was diluted to a final volume of 68.5 μL or 67 μL, allowed to react at 65° C. for 10 minutes, and then cooled on ice, and premixes were prepared as shown in Tables 3 and 4 below.

TABLE 3

Premix for ScriptCap ™ M7G Capping
System kit for Cap-0 capping

| | |
|---|---|
| 10X ScriptCap Capping Buffer | 10 μL |
| 10 mM GTP | 10 μL |
| 2 mM SAM | 5 μL |
| ScriptGuard RNase inhibitor | 2.5 μL |
| ScriptCap Capping Enzyme (10 U/mL) | 4 μL |
| Total volume | 31.5 μL |

TABLE 4

Premix for ScriptCap ™ Cap-1 Capping
System kit for Cap-1 capping

| | |
|---|---|
| 10X ScriptCap Capping Buffer | 10 μL |
| 10 mM GTP | 10 μL |
| 20 mM SAM | 2.5 μL |
| ScriptGuard RNase inhibitor | 2.5 μL |
| ScriptCap 2'-O-Methyltransferase (100 U/mL) | 4 μL |
| ScriptCap Capping Enzyme (10 U/mL) | 4 μL |
| Total volume | 33 μL |

Uncapped RNA was added to the prepared premix solution and allowed to react at 37° C. for 30 minutes, after which Cap-0- and Cap-1-RNA were purified using lithium chloride (LiCl).

The LiCl purification method was performed in a manner in which a mixed solution obtained by mixing a 7.5 M LiCl solution (ThermoFisher), nuclease-free purified water, and the RNA solution at 1:1:1 was allowed to react at −20° C. for 30 minutes and then centrifuged at 13000 rpm for 15 minutes, after which the supernatant was removed, and the pellets were added with 70% ethanol, followed by centrifugation at 13000 rpm for 5 minutes, after which the supernatant was removed, and the RNA pellets were then lysed in nuclease-free purified water, thereby obtaining purified RNA.

Example 3: Introduction of mRNA into Mammalian Cells and Expression of Protein of Interest 293T cells (ATCC CRL-3216) were seeded to 70-80% confluency in a 6-well plate, followed by culture overnight in a DMEM/HIGH GLUCOSE (HyClone™) medium. Each of 2.5 μg of the in-vitro transcript MRNA obtained in Example 2 and 5 UL of Lipofectamine TM2000 (ThermoFisher Scientific, USA) was mixed with 200 μL of Opti-MEM™ (ThermoFisher Scientific, USA), followed by reaction at room temperature for 10 minutes, after which the two solutions were mixed to afford a mixed solution, which was then allowed to react at room temperature for 5 minutes.

The cell culture medium of 293T cells cultured in the 6-well plate was replaced with a DMEM/HIGH GLUCOSE (HyClone™) medium without serum or antibiotics, after which the mixed solution was added thereto. After 4 hours, the culture medium was replaced with a medium containing 10% fetal bovine serum (HyClone™) and 1% antibiotics (HyClone™), followed by culture for 24 hours. After culture for 24 hours, the cells were washed with DPBS, added with a RIPA buffer (Biosesang, Korea) containing a protease inhibitor (Roche, Basel, Swiss), and lysed at 4° C. for 30 minutes. After cell lysis, centrifugation was performed at 13000 rpm for 30 minutes, after which the supernatant was separated, and the protein was quantified through a BCA assay. Each lysate sample that was quantified was added with a 5×SDS-PAGE sample buffer and boiled at 100° ° C. for 10 minutes. Proteins were classified by size through SDS-PAGE, transferred to a PVDF membrane, added with 10 mL of 5% BSA+5% skim milk (in phosphate buffer containing 0.1% Tween-20), and allowed to react at 4° C. overnight. Thereafter, 10 mL of a 1:5000 dilution of anti PA-D4 antibody (ABION, Seoul, South Korea, in dilution buffer, 5% skim milk in phosphate buffer containing 0.1% Tween-20) was added thereto, followed by reaction at room temperature for 3 hours. After washing with a 0.1% Tween-20 phosphate buffer, HRP-conjugated goat anti-mouse IgG (H+L) (ThermoFisher Scientific, MA, USA) was added to the membrane, followed by reaction at room temperature for 1 hour. Finally, washing and then development using an EZ-Western Lumi Femto solution (DOGEN, Seoul, South Korea) were performed, whereby the protein band of interest expressed from the in-vitro transcript mRNA was identified.

Example 4: Expression Confirmation Method Using Real-Time Fluorescence Analysis 293T cells (ATCC CRL-3216) were seeded to 70-80% confluency in a 6-well plate, followed by culture overnight. Each of 2.5 μg of the in-vitro transcript mRNA obtained in Example 2 and 5 μL of Lipofectamine TM2000 (Ther-moFisher Scientific, USA) was mixed with 200 μL of Opti-MEM™ (Thermo Fisher Scientific, USA) and allowed to react at room temperature for 10 minutes, after which the two solutions were mixed to obtain a mixed solution, followed by reaction at room temperature for 5 minutes.

The cell culture medium of 293T cells cultured in the 6-well plate was replaced with a DMEM/HIGH GLUCOSE (HyClone™) medium without serum or antibiotics, and then the mixed solution was added thereto. The cell culture plate was placed in IncuCyte™ (Sartorius, Germany) and red fluorescence was measured every hour. After 4 hours, the culture medium was replaced with a medium containing 10% fetal bovine serum (HyClone™) and 1% antibiotics (HyClone™), followed by culture for 48 hours.

Example 5: Optimization of Poly(A) Tail of In-Vitro Transcript mRNA

A poly(A) tail is a component located at the 3' end of the in-vitro transcript mRNA of the present invention. Along with the 5' cap, the poly(A) tail serves to protect mRNA from enzymatic degradation, and when the length thereof is insufficient, it is known that the stability of mRNA is deteriorated. The poly(A) tail also affects translation. PABP (poly(A)-binding protein), which is a protein that binds to the poly(A) tail, binds to eIF4G (eukaryote translation initiation factor 4 G) during initiation of translation to thus attach the 40S ribosomal subunit to mRNA.

In order to determine the poly(A) tail optimal for the in-vitro transcript mRNA platform for delivery of the gene of interest to animal cells and expression thereof, various types of mRNA were produced through in-vitro transcription depending on 1) the length of the poly(A) tail, 2) the shape of the end thereof, and 3) whether a non-A residue was mixed, and the expression level of the protein of interest was compared.

1) Length of Poly(A) Tail

In order to compare the translation efficiency of mRNA depending on changes in the length of the poly(A) tail, template DNA having each of a conventional $A_{33}C_{18}$ tail, as well as $A_0$, $A_{30}$, and $A_{120}$ tails respectively containing 0, 30, and 120 adenines, was constructed. Using each template DNA, mRNA was synthesized by performing in-vitro tran-scription and Cap-1 capping in the same manner as in Example 2, and the expression level of the protein of interest in 293T cells was compared in the same manner as in Example 3.

Consequently, as shown in FIG. 3, IgM-D4 expression was not observed in the $A_0$ tail, and it was confirmed that expression was best for the $A_{120}$ tail, sequentially followed by the $A_{30}$ tail and the $A_{33}C_{18}$ tail. This is considered to be because the time required for disappearance of the A tail is increased due to deadenylation with an increase in the length of the tail, resulting in relatively high stability, and the protein PABP binds better with an increase in the length of the tail, thereby increasing translation efficiency.

2) Shape of End

Since a linearized DNA template is used upon in-vitro transcription, the end of the poly(A) tail of mRNA that is produced may be terminated with residue A or may include a restriction enzyme recognition site, depending on the restriction enzyme used for linearization of the template plasmid DNA.

12

In order to compare the extent of translation depending on the shape of the end of the poly(A) tail, non-complete or complete end mRNA was synthesized based on a template linearized with an NheI or SapI restriction enzyme, and the expression level of the protein of interest in 293T cells was compared in the same manner as in Example 3.

Consequently, as shown in FIG. 4, it was confirmed that the expression efficiency of mRNA having a tail the end of which is terminated with A alone was superior. This is deemed to be because the non-complete tail including a portion of the restriction enzyme recognition site does not properly block 3'->5' exonuclease, unlike the complete poly (A) tail.

3) Mixing of Non-Adenine NT (Non-A Residue)

In order to compare the translation efficiency of the non-A residue-mixed tail, with reference to a publication reporting that non-A residue included in the A tail by TENT4A or 4B interferes with deadenylase action, template DNA having each of the original $A_{120}$ tail, the $A_{120}$-G-mixed Tail, the $A_{120}$-C-mixed tail, and the $A_{120}$-U-mixed tail was con-structed. In-vitro transcript mRNA was synthesized using each template, and the expression level of the protein of interest in 293T cells was compared in the same manner as in Example 3.

Consequently, it was confirmed that the expression effi-ciency of the U-mixed tail mRNA was the best. In the case of G- and C-mixed tails and the original tail, the expression efficiency of the original tail was consistently observed to be the worst in real-time fluorescence detection results, but this result was not consistently obtained in the Western blot results. However, in all experiments, the expression effi-ciency of the $A_{120}$-U-mixed tail was the greatest, and when non-A residue is present in the poly(A) tail, deadenylase action is inhibited, based on which U was determined to very efficiently inhibit the enzyme action.

Example 6: Optimization of 5' Cap of In-Vitro Transcript mRNA

A 5' cap is a component located at the 5' start site of mRNA. Like the poly(A) tail, a 5' cap is known to play a role in preventing mRNA degradation. The 5' cap also affects translation. During initiation of translation, the 5' cap binds to eIF4E (eukaryote translation initiation factor 4 E) to thus attach the 40S ribosomal subunit to mRNA.

In order to determine the 5' cap optimal for the in-vitro transcript mRNA platform for delivery of the gene of interest to animal cells and expression thereof, in-vitro transcript mRNA having each of no cap, Cap-0, Cap-1, and ARCA was synthesized, and the expression level of the protein of interest in 293T cells was compared in the same manner as in Example 3.

Consequently, as shown in FIG. 6, it was confirmed that the expression efficiency of ACRA and Cap-1 was the greatest. However, in the method for performing in-vitro transcription and capping at the same time by decreasing the GTP ratio and increasing the cap analog ratio, like ARCA, uncapped RNA may be synthesized. Since this is capable of inducing innate immunity, Cap-1, which is the post-transcriptional capping system using an enzyme, was determined to be more suitable for the in-vitro transcript mRNA platform.

Example 7: Substitution with Modified Nucleotide for Optimization of In-Vitro Transcript mRNA It is known that the use of a modified nucleotide is capable of evading the innate immune sensor in the host and increasing translation activity.

In order to determine the modified nucleotide suitable for the in-vitro transcript mRNA platform for delivery of a gene of interest to animal cells and expression thereof, in-vitro transcript mRNA including each of modified CTP (5-methylcytidine-5'-triphosphate (TriLink Bio Technologies)), modified UTP (pseudouridine-5'-triphosphate (TriLink Bio Technologies)), and N1-methylpseudouridine-5'-triphosphate (TriLink Bio Technologies) was synthesized, and the expression level of the protein of interest in 293T cells was compared in the same manner as in Example 3.

Consequently, as shown in FIG. 7, it was confirmed that mRNA in which U of mRNA was 100% substituted with modified U using modified UTP alone exhibited the highest protein expression efficiency. Moreover, since use thereof with the U-mixed tail having excellent protein expression efficiency among the mixed tails of Example 4 is judged to exhibit a synergistic effect, the results for the mixed tail using modified UTP were compared, and it was found that protein expression in the U-mixed tail using modified U was the greatest, as expected. It is assumed that modified UTP plays an important role in stabilizing the mRNA structure.

INDUSTRIAL APPLICABILITY

According to the present invention, when the in-vitro transcript mRNA including a gene of interest according to the present invention is introduced into animal cells, a large amount of a protein of interest can be expressed in the animal cells, so the in-vitro transcript mRNA of the present invention can be used in a genetic vaccine for treatment of autoimmune diseases, infectious diseases, cancer- or tumor-related diseases, and inflammatory diseases.

Although specific embodiments of the present invention have been disclosed in detail above, it will be obvious to those skilled in the art that the description is merely of preferable exemplary embodiments and is not to be construed as limiting the scope of the present invention. Therefore, the substantial scope of the present invention will be defined by the appended claims and equivalents thereof. Simple modifications or changes of the present invention can be easily used by those of ordinary skill in the art, and all such modifications or changes can be considered to be included in the scope of the present invention.

SEQUENCE LIST FREE TEXT

An electronic file is attached.

The invention claimed is:

1. An in-vitro transcript mRNA, comprising;
   (a) an RNA sequence insertion portion encoding a peptide of interest or a protein of interest;
   (b) 5'-UTR and 3'-UTR linked to both ends of an RNA sequence encoding the peptide of interest or the protein of interest;
   (c) a 5' cap linked to 5'-UTR;
   (d) a poly (A) tail containing 20 to 400 adenines linked to 3'-UTR, and
   wherein the poly (A) tail contains uracil, in which the uracil is inserted between 2 to 20 adenines of the poly (A) tail, and an end of the poly (A) tail is adenine.

2. The in-vitro transcript mRNA according to claim 1, wherein the poly (A) tail contains 30 to 200 adenines.

3. The in-vitro transcript mRNA according to claim 1, wherein the 5' cap is Cap-1 or ARCA (anti-reverse cap analog).

4. The in-vitro transcript mRNA according to claim 1, wherein all or part of uracil (U) in an in-vitro transcript mRNA sequence is substituted with modified U.

5. The in-vitro transcript mRNA according to claim 4, wherein modified UTP is pseudo UTP or N1-methylpseudo UTP.

6. The in-vitro transcript mRNA according to claim 1, wherein the peptide of interest or the protein of interest is a therapeutically active protein or peptide, adjuvant protein, antigen, tumor antigen, pathogenic antigen, animal antigen, viral antigen, protozoan antigen, bacterial antigen, allergic antigen, autoimmune antigen, allergen, antibody, immunostimulatory protein or peptide, or antigen-specific T-cell receptor.

7. A template DNA for in-vitro transcript mRNA production, comprising:
   (a) a portion having a DNA sequence corresponding to the RNA in-vitro transcript mRNA according to claim 1; and
   (b) a promoter to which RNA polymerase binds for transcription of the DNA sequence corresponding to the in-vitro transcript mRNA.

8. The template DNA according to claim 7, wherein the promoter is selected from the group consisting of a T7 promoter, a T3 promoter, and an SP6 promoter.

9. The template DNA according to claim 7, comprising a restriction enzyme recognition site linked to a poly (A) tail included in the portion having the DNA sequence corresponding to the in-vitro transcript mRNA.

10. A pharmaceutical composition for a vaccine comprising the in-vitro transcript mRNA according to claim 1.

* * * * *

SEQUENCE LISTING

```
<160> NUMBER OF SEQ ID NOS: 5

<210> SEQ ID NO 1
<211> LENGTH: 1431
<212> TYPE: DNA
<213> ORGANISM: Artificial Sequence
<220> FEATURE:
<223> OTHER INFORMATION: Synthetic construct

<400> SEQUENCE: 1
atggtgagca agggcgagga ggtcatcaaa gagttcatgc gcttcaaggt gcgcatggag      60
ggctccatga acggccacga gttcgagatc gagggcgagg gcgagggccg cccctacgag     120
ggcacccaga ccgccaagct gaaggtgacc aagggcggcc ccctgccctt cgcctgggac     180
atcctgtccc cccagttcat gtacggctcc aaggcgtacg tgaagcaccc cgccgacatc     240
cccgattaca agaagctgtc cttccccgag ggcttcaagt gggagcgcgt gatgaacttc     300
gaggacggcg gtctggtgac cgtgacccag gactcctccc tgcaggacgg cacgctgatc     360
tacaaggtga agatgcgcgg caccaacttc ccccccgacg gccccgtaat gcagaagaag     420
accatgggct gggaggcctc caccgagcgc ctgtaccccc gcgacggcgt gctgaagggc     480
gagatccacc aggccctgaa gctgaaggac ggcggccact acctggtgga gttcaagacc     540
atctacatgg ccaagaagcc cgtgcaactg cccggctact actacgtgga caccaagctg     600
gacatcacct cccacaacga ggactacacc atcgtggaac agtacgagcg ctccgagggc     660
cgccaccacc tgttcctggg gcatggcacc ggcagcaccg gcagcggcag ctccggcacc     720
gcctcctccg aggacaacaa catggccgtc atcaaagagt tcatgcgctt caaggtgcgc     780
atggagggct ccatgaacgg ccacgagttc gagatcgagg gcgagggcga gggccgcccc     840
tacgagggca cccagaccgc caagctgaag gtgaccaagg gcggcccect gcccttcgcc     900
```

```
tgggacatcc tgtcccccca gttcatgtac ggctccaagg cgtacgtgaa gcaccccgcc      960
gacatccccg attacaagaa gctgtccttc cccgagggct tcaagtggga gcgcgtgatg     1020
aacttcgagg acggcggtct ggtgaccgtg acccaggact cctccctgca ggacggcacg     1080
ctgatctaca aggtgaagat gcgcggcacc aacttccccc ccgacggccc cgtaatgcag     1140
aagaagacca tgggctggga ggcctccacc gagcgcctgt accccgcga cggcgtgctg      1200 aagggcgaga tccaccaggc cctgaagctg aaggacggcg ccactacct ggtggagttc      1260 aagaccatct acatggccaa gaagcccgtg caactgcccg ctactacta cgtggacacc     1320 aagctggaca tcacctccca caacgaggac tacaccatcg tggaacagta cgagcgctcc     1380
gagggccgcc accacctgtt cctgtacggc atggacgagc tgtacaagta a             1431

<210> SEQ ID NO 2
<211> LENGTH: 1610
<212> TYPE: DNA
<213> ORGANISM: Artificial Sequence
<220> FEATURE:
<223> OTHER INFORMATION: Synthetic construct

<400> SEQUENCE: 2
ggttccgcgc acatttcccc gaaaagtgcc acctgacgtc taagaaacca ttattatcat       60
gacattaacc tataaaaata ggcgtatcac gaggcccttt cgtctcgcgc gtttcggtga      120
tgacggtgaa aacctctgac acatgcagct cccggagacg tcacagctt gtctgtaagc       180 ggatgccggg agcagacaag cccgtcaggg cgcgtcagcg ggtgttggcg ggtgtcgggg      240
ctggcttaac tatgcggcat cagagcagat tgtactgaga gtgcaccata tgcggtgtga      300
aataccgcac agatgcgtaa ggagaaaata ccgcatcagg cgccattcgc cattcaggct      360
gcgcaactgt tgggaagggc gatcggtgcg ggcctcttcg ctattacgcc agctggcgaa      420 aggggatgt gctgcaaggc gattaagttg ggtaacgcca gggttttccc agtcacgacg        480
ttgtaaaacg acggccagtg aattgtaata cgactcacta tagggcgaat taattcgagc      540
tcggtaccca gcttgcttgt tcttttttgca gaagctcaga ataaacgctc aactttggca     600
gatcaattcc ccatcatcga tgaattcgcc accatgaaat tcagctgggt catgttcttc      660
ctgatggcag tggttacagg ggtcaattca gagaagatca agctgaatgc caagatgaat      720
atcctgatcc gggacaagag attccactac gataggaaca acatcgccgt gggcgccgac      780
gagagcgtgg tgaaggaggc ccacagagaa gtgattaact cttctaccga gggactgctg      840
ctgaacattg acaaggacat ccggaagatc ctgagcggct atatcgtgga gatcgaggat      900
accgagggcc tgaaagaagt gatcaatgac agatacgaca tgctgaacat cagcagcctg      960
cggcaggatg gcaagacctt tatcgacttc aaaaaataca atgataagct gccactgtac     1020
atcagcaacc ccaactataa ggtgaacgtg tacgccgtga caaaggagaa taccatcatc     1080
aatccttccg agaacggcga taccagcacc aatggcatta gaagattct gattttcagc      1140 aaaaagggat acgaaatcgg ctgaaagctt gatctggtta ccactaaacc agcctcaaga     1200
acacccgaat ggagtctcta agctacataa taccaactta cactttacaa aatgttgtcc     1260
cccaaaatgt agccattcgt atctgctcct aataaaaaga aagtttcttc acattctaaa     1320
aaaaaataaa aaaaataaa aaaaaataaa aaaaaataaa aaaaaataaa aaaaaataaa      1380
aaaaaataaa aaaaaataaa aaaaaataaa aaaaaataaa aaaaaataaa aaaaaacga      1440 agagctagct taagtattct atagtgtcgc ttcctcgctc actgactcgc tgcgctcggt     1500
cgttcggctg cggcgagcgg tatcagctca ctcaaaggcg gtaatacggt tatccacaga     1560
```

-continued

```
atcaggggat aacgcaggaa agaacatgtg agcaaaaggc cagcaaaagg              1610

<210> SEQ ID NO 3
<211> LENGTH: 34
<212> TYPE: DNA
<213> ORGANISM: Artificial Sequence
<220> FEATURE:
<223> OTHER INFORMATION: Synthetic construct

<400> SEQUENCE: 3
atgaattcgc caccatggtg agcaagggcg agga                                  34

<210> SEQ ID NO 4
<211> LENGTH: 28
<212> TYPE: DNA
<213> ORGANISM: Artificial Sequence
<220> FEATURE:
<223> OTHER INFORMATION: Synthetic construct

<400> SEQUENCE: 4
ataagctttt acttgtacag ctcgtcca                                         28

<210> SEQ ID NO 5
<211> LENGTH: 1815
<212> TYPE: DNA
<213> ORGANISM: Artificial Sequence
<220> FEATURE:
<223> OTHER INFORMATION: Synthetic construct

<400> SEQUENCE: 5
gggcgaatta attcgagctc ggtacccagc ttgcttgttc tttttgcaga agctcagaat       60
aaacgctcaa ctttggcaga tcaattcccc atcatcgatg aattcgccac catggtgagc      120
aagggcgagg aggtcatcaa agagttcatg cgcttcaagg tgcgcatgga gggctccatg      180
aacggccacg agttcgagat cgagggcgag ggcgagggcc gcccctacga gggcacccag      240
accgccaagc tgaaggtgac caagggcggc cccctgccct tcgcctggga catcctgtcc      300
ccccagttca tgtacggctc caaggcgtac gtgaagcacc ccgccgacat ccccgattac      360
aagaagctgt ccttccccga gggcttcaag tgggagcgcg tgatgaactt cgaggacggc      420
ggtctggtga ccgtgaccca ggactcctcc ctgcaggacg gcacgctgat ctacaaggtg      480
aagatgcgcg gcaccaactt cccccccgac ggccccgtaa tgcagaagaa gaccatgggc      540
tgggaggcct ccaccgagcg cctgtacccc cgcgacggcg tgctgaaggg cgagatccac      600
caggccctga gctgaagga cggcggccac tacctggtgg agttcaagac catctacatg      660
gccaagaagc ccgtgcaact gcccggctac tactacgtgg acaccaagct ggacatcacc      720
tcccacaacg aggactacac catcgtggaa cagtacgagc gctccgaggg ccgccaccac      780
ctgttcctgg ggcatggcac cggcagcacc ggcagcggca gctccggcac cgcctcctcc      840
gaggacaaca acatggccgt catcaaagag ttcatgcgct tcaaggtgcg catggagggc      900
tccatgaacg gccacgagtt cgagatcgag ggcgagggcg agggccgccc ctacgagggc      960
acccagaccg ccaagctgaa ggtgaccaag ggcggccccc tgcccttcgc ctgggacatc     1020
ctgtcccccc agttcatgta cggctccaag gcgtacgtga gcacccccgc cgacatcccc     1080
gattacaaga agctgtcctt ccccgagggc ttcaagtggg agcgcgtgat gaacttcgag     1140
gacggcggtc tggtgaccgt gacccaggac tcctccctgc aggacggcac gctgatctac     1200
aaggtgaaga tgcgcggcac caacttcccc cccgacggcc ccgtaatgca gaagaagacc     1260
```

-continued

```
atgggctggg aggcctccac cgagcgcctg taccccgcg acggcgtgct gaagggcgag    1320
atccaccagg ccctgaagct gaaggacggc ggccactacc tggtggagtt caagaccatc    1380
tacatggcca agaagcccgt gcaactgccc ggctactact acgtggacac caagctggac    1440
atcacctccc acaacgagga ctacaccatc gtggaacagt acgagcgctc cgagggccgc    1500
caccacctgt tcctgtacgg catggacgag ctgtacaagt aaaagcttga tctggttacc    1560
actaaaccag cctcaagaac acccgaatgg agtctctaag ctacataata ccaacttaca    1620
ctttacaaaa tgttgtcccc caaaatgtag ccattcgtat ctgctcctaa taaaaagaaa    1680
gtttcttcac attctaaaaa aaaataaaaa aaaataaaaa aaaataaaaa aaaataaaaa    1740
aaaataaaaa aaaataaaaa aaaataaaaa aaaataaaaa aaaataaaaa aaaataaaaa    1800
aaaataaaaa aaaaa                                                     1815
```